US010547032B2

(12) United States Patent
Lee et al.

(10) Patent No.: US 10,547,032 B2
(45) Date of Patent: Jan. 28, 2020

(54) FILM COMPRISING GRAPHENE OXIDE AND CLAY, PREPARATION METHOD THEREFOR, AND USE THEREOF AS OXYGEN BARRIER FILM

(71) Applicant: Korea Institute of Industrial Technology, Cheonan-si (KR)

(72) Inventors: Sang Bong Lee, Anyang-si (KR); Jin Kie Shim, Seoul (KR); Jong Tae Yoo, Bucheon-si (KR)

(73) Assignee: LOREA INSTITUTE OF INDUSTRIAL TECHNOLOGY, Cheonan-si (KR)

( * ) Notice: Subject to any disclaimer, the term of this patent is extended or adjusted under 35 U.S.C. 154(b) by 191 days.

(21) Appl. No.: 15/329,556

(22) PCT Filed: Oct. 17, 2014

(86) PCT No.: PCT/KR2014/009779
§ 371 (c)(1),
(2) Date: Jan. 26, 2017

(87) PCT Pub. No.: WO2016/017857
PCT Pub. Date: Feb. 4, 2016

(65) Prior Publication Data
US 2018/0212209 A1    Jul. 26, 2018

(30) Foreign Application Priority Data
Jul. 31, 2014  (KR) .................. 10-2014-0098241

(51) Int. Cl.
*H01M 2/02* (2006.01)
*B01D 71/00* (2006.01)
(Continued)

(52) U.S. Cl.
CPC ........ *H01M 2/0287* (2013.01); *B01D 53/228* (2013.01); *B01D 67/0039* (2013.01); *B01D 69/12* (2013.01); *B01D 71/00* (2013.01); *B01D 71/02* (2013.01); *B01D 71/021* (2013.01); *B01D 71/024* (2013.01); *B65D 65/42* (2013.01); *H01M 2/0292* (2013.01); *G01L 9/0041* (2013.01); *G01N 33/00* (2013.01); *H01L 23/291* (2013.01);
(Continued)

(58) Field of Classification Search
None
See application file for complete search history.

(56) References Cited

U.S. PATENT DOCUMENTS

2009/0295103 A1* 12/2009 Ebina .................. B32B 18/00
                                                        277/650
2014/0141255 A1*  5/2014 Kano .................. C23C 16/0245
                                                       428/423.5

FOREIGN PATENT DOCUMENTS

GB      201401506    *  3/2014
GB      2522626 A    *  8/2015
(Continued)

OTHER PUBLICATIONS

International Search Report, dated Apr. 23, 2015, for International Application No. PCT/KR2014/009779, 2 pages.

*Primary Examiner* — Jonathan Crepeau
(74) *Attorney, Agent, or Firm* — Cantor Colburn LLP

(57) ABSTRACT

The present invention relates to a film comprising graphene oxide (GO) and clay, an electronic device comprising the film, a packaging material coated with the film, and a preparation method thereof.

11 Claims, 8 Drawing Sheets

(51) Int. Cl.
    *H01L 31/048*      (2014.01)
    *H01L 51/52*      (2006.01)
    *B01D 71/02*      (2006.01)
    *B01D 53/22*      (2006.01)
    *B01D 67/00*      (2006.01)
    *B01D 69/12*      (2006.01)
    *B65D 65/42*      (2006.01)
    *G01L 9/00*      (2006.01)
    *G01N 33/00*      (2006.01)
    *H01L 23/29*      (2006.01)

(52) U.S. Cl.
    CPC ...... *H01L 31/0481* (2013.01); *H01L 51/5253* (2013.01)

(56) References Cited

FOREIGN PATENT DOCUMENTS

| | | |
|---|---|---|
| JP | 2013-52680 A | 3/2013 |
| JP | 2014-1098 A | 1/2014 |
| KR | 10-2009-0093946 A | 9/2009 |
| KR | 10-2013-0125668 A | 11/2013 |
| KR | 10-2014-0043747 A | 4/2014 |

\* cited by examiner

[FIG. 1]
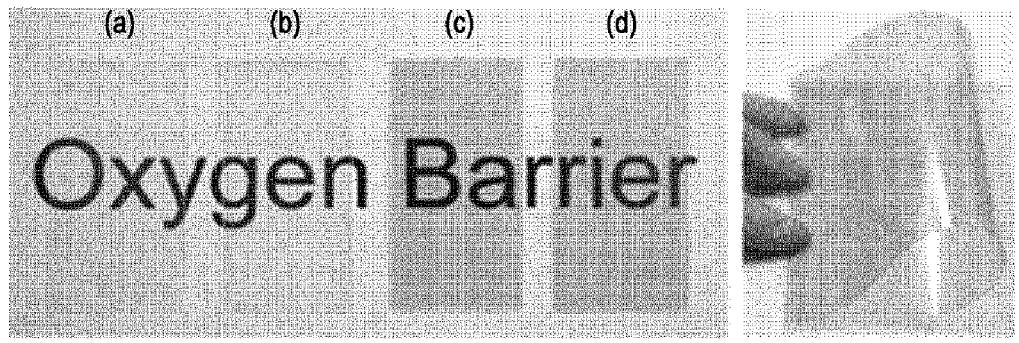
[FIG. 2]
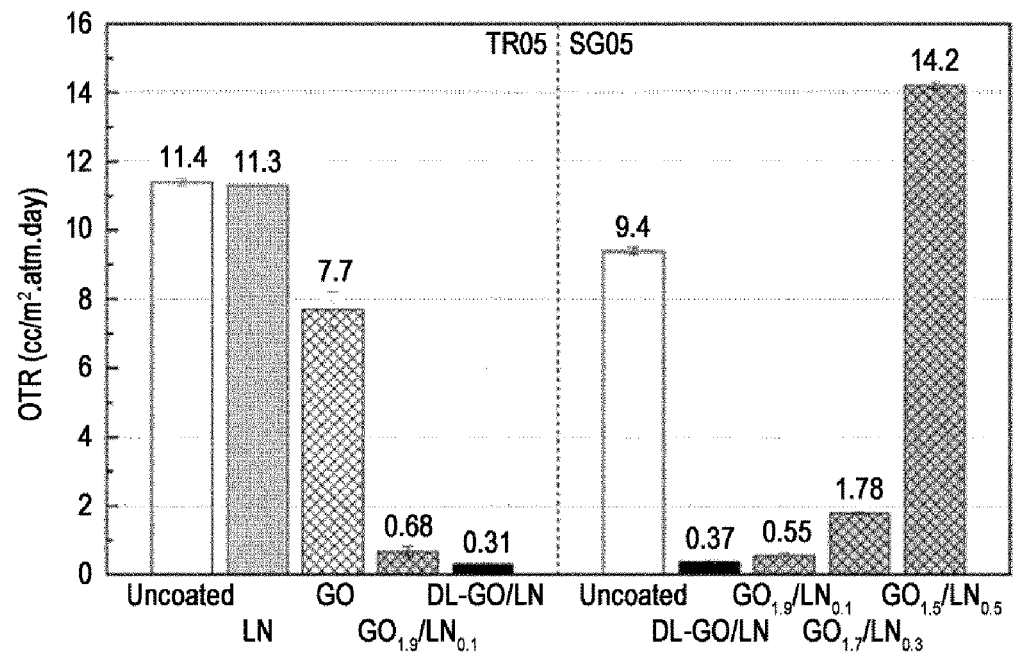

[FIG. 3]
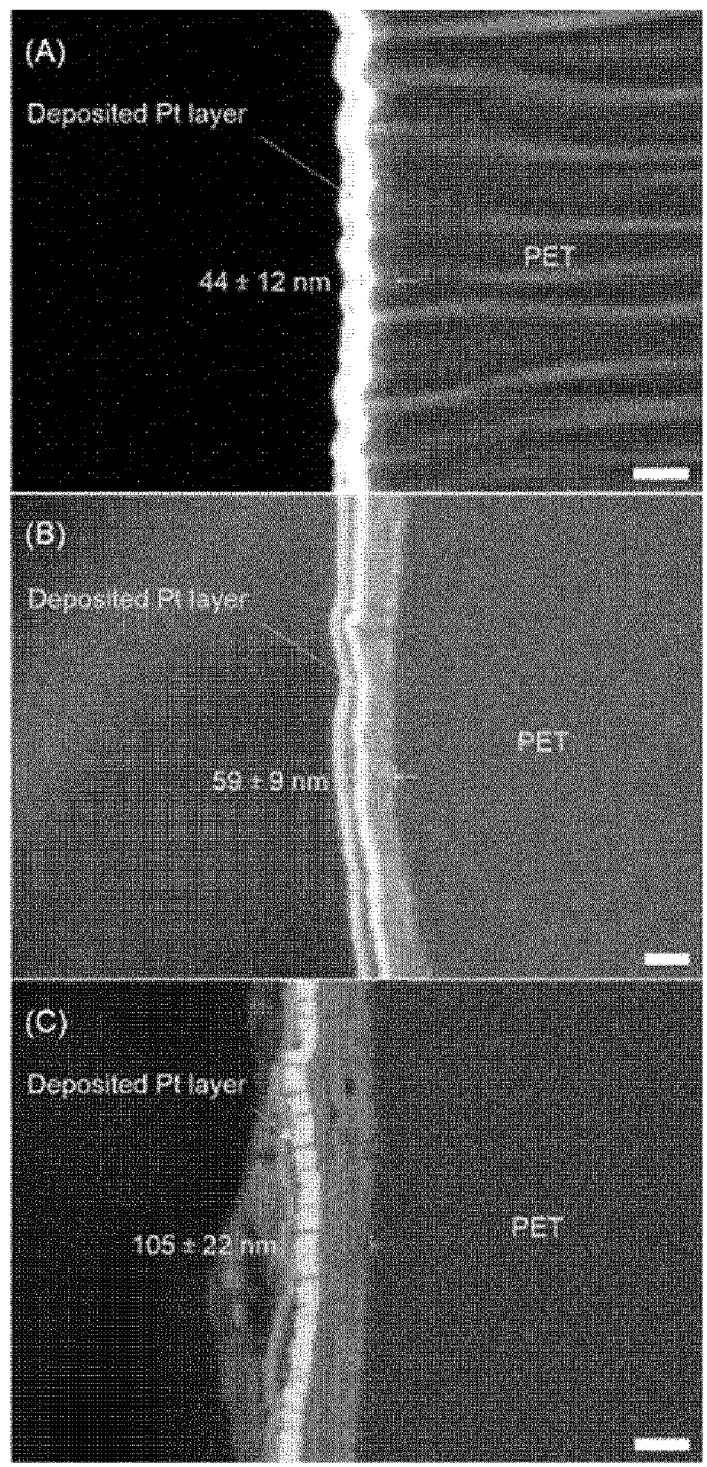

[FIG. 4]
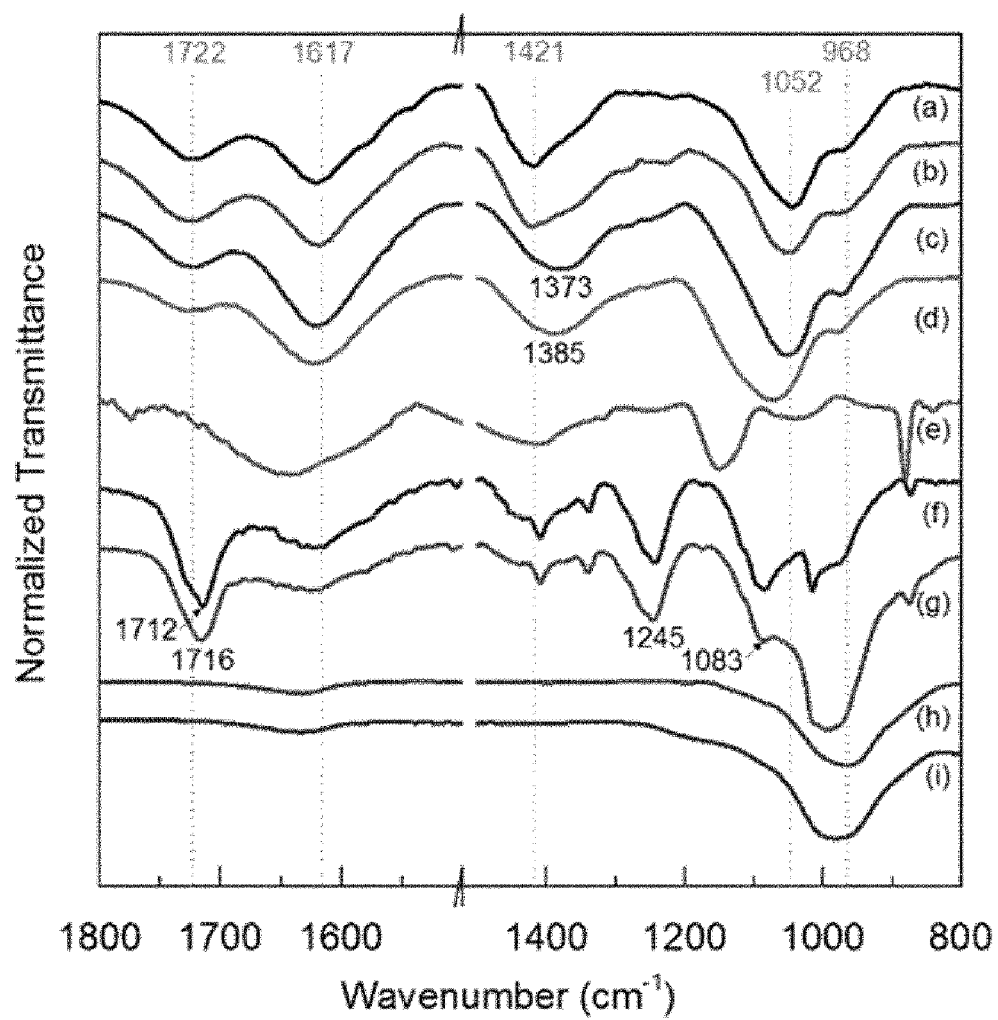

[FIG. 5]
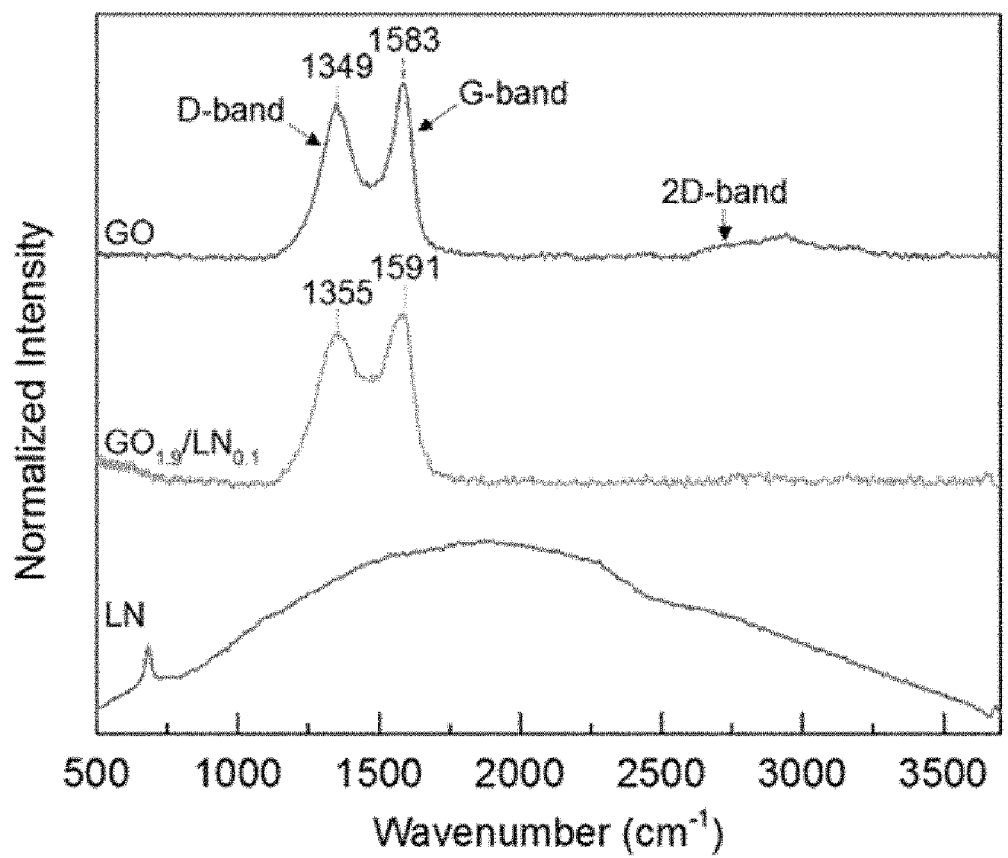

[FIG. 6]
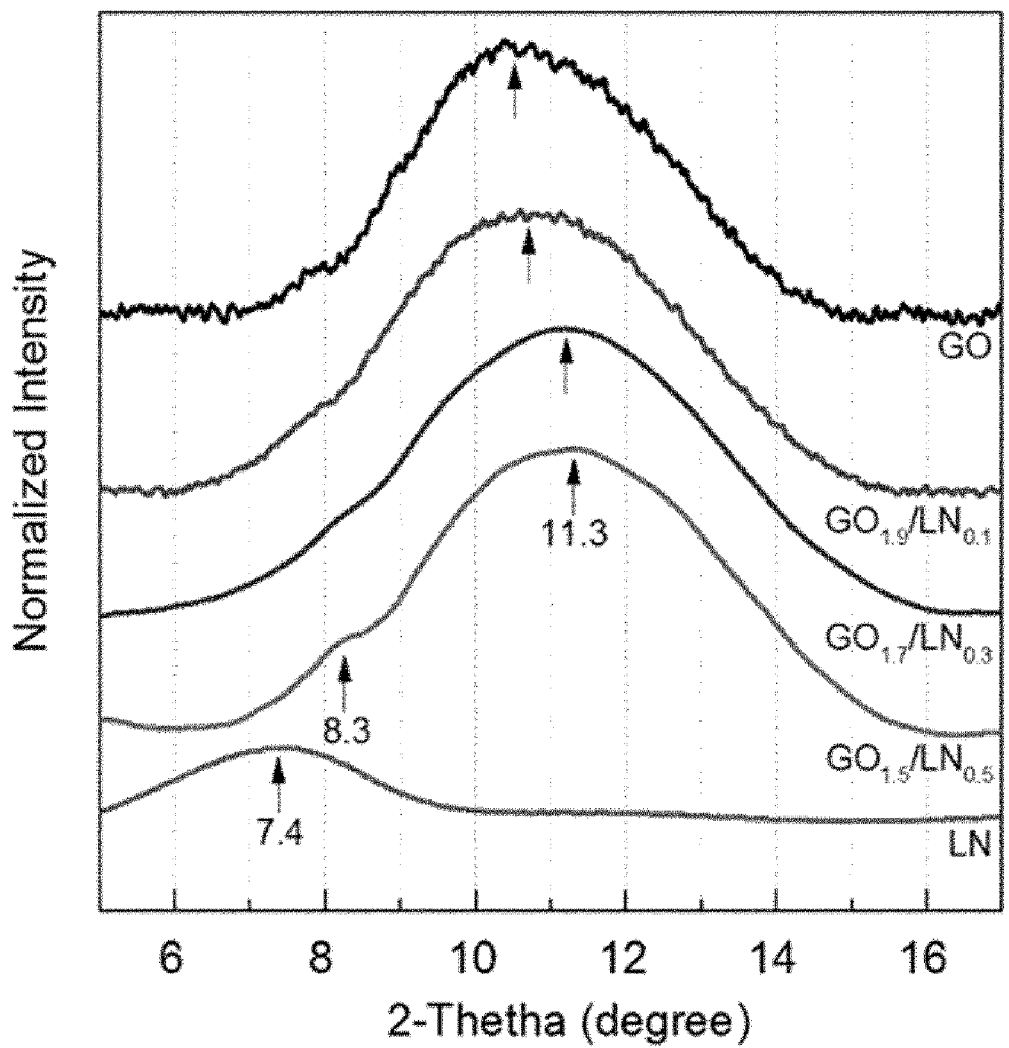

[FIG. 7]
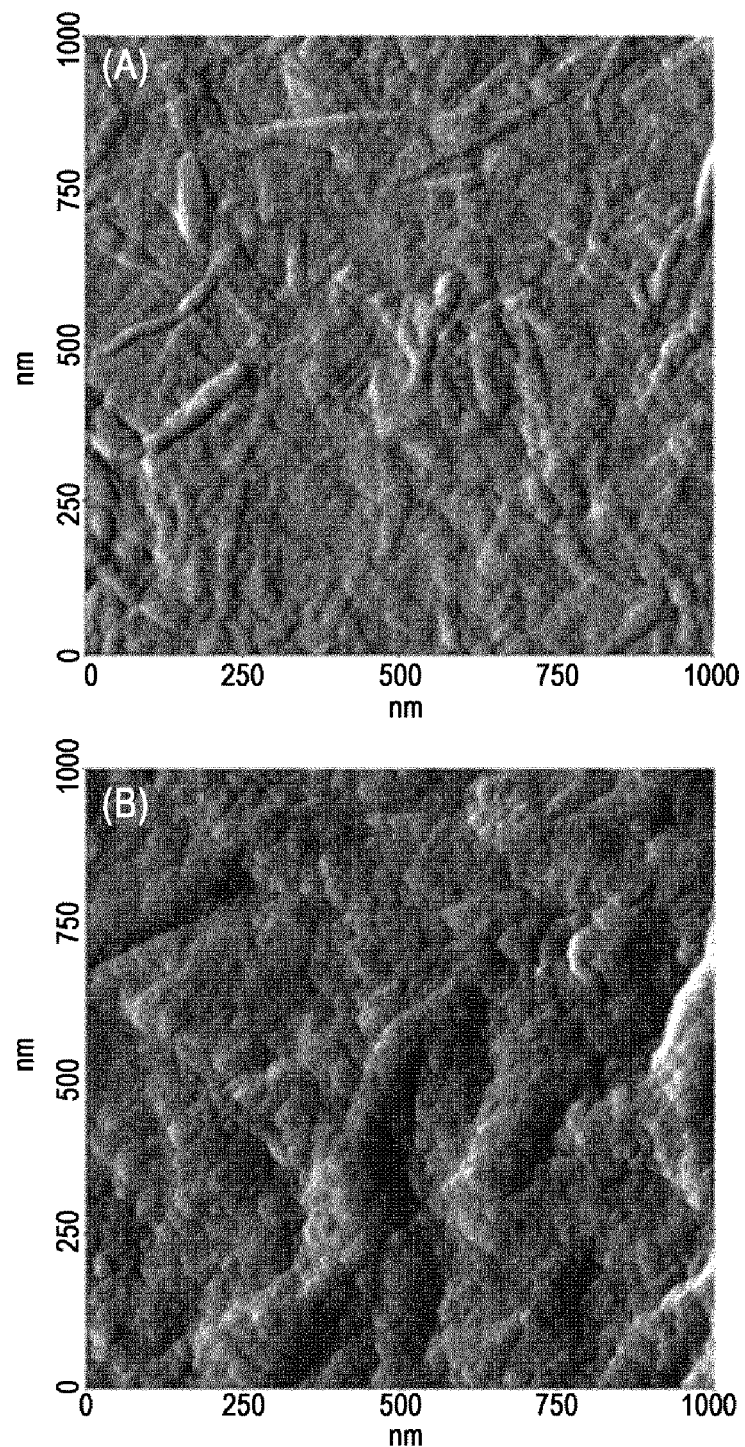

[FIG. 8]
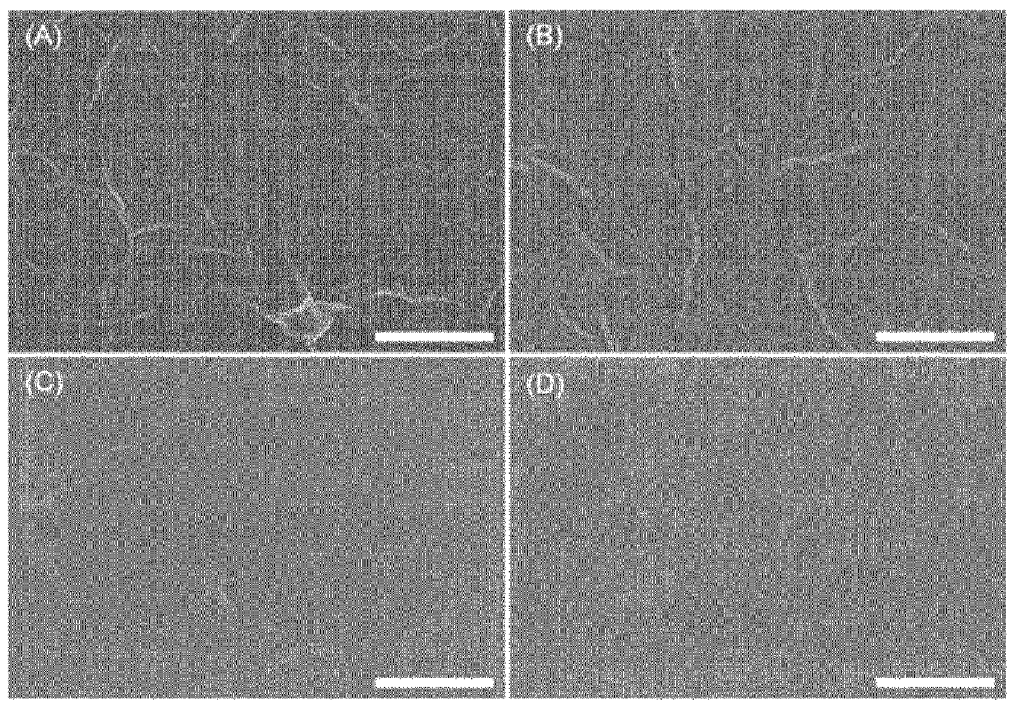

[FIG. 9]
(A)
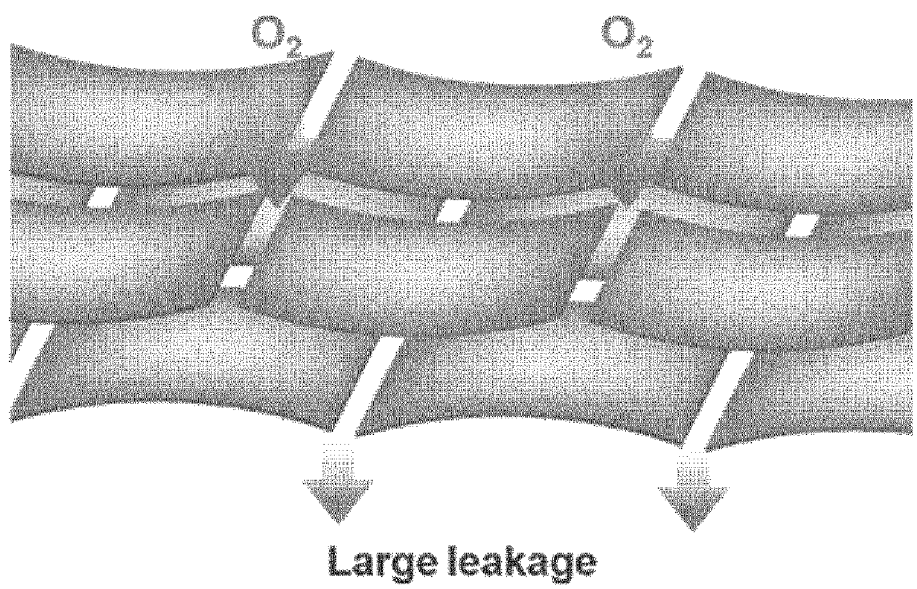
(B)
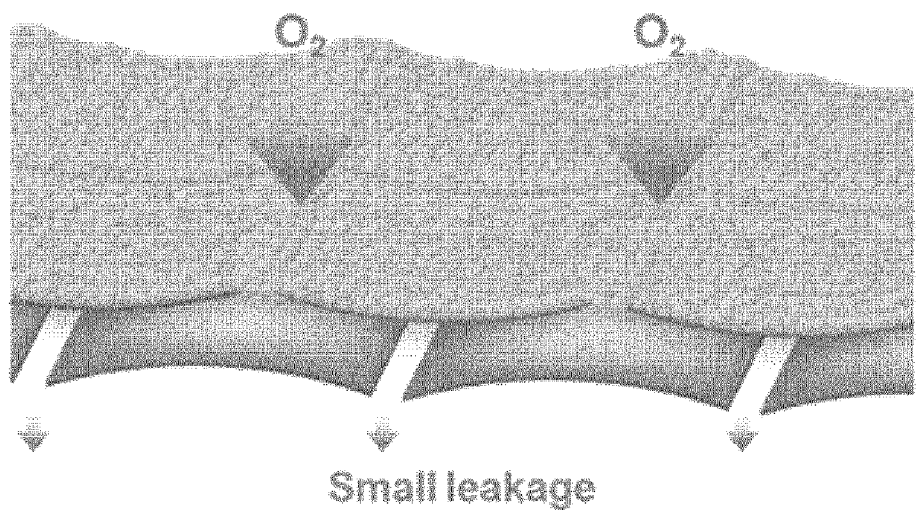

FILM COMPRISING GRAPHENE OXIDE AND CLAY, PREPARATION METHOD THEREFOR, AND USE THEREOF AS OXYGEN BARRIER FILM

TECHNICAL FIELD

The present invention relates to a film comprising graphene oxide (GO) and clay, an electronic device comprising the film as an oxygen barrier film, a packaging material coated with the film, and a method for preparing the same.

BACKGROUND ART

Gas barrier films designed to block active gases are one of the most important topics in many application areas such as solar cells and electronic devices, as well as food packaging. In general, in order to prepare a gas barrier film, aluminum is vacuum deposited on a polymer film substrate (PET, OPP, CPP, LDPE, etc.), or methods of depositing or coating with an inorganic material such as silica or alumina, and of depositing a polymer film having excellent gas barrier properties such as ethylene vinyl alcohol copolymer (EVOH), nylon, polyacrylonitrile, and polyvinylidene chloride (PVDC) are used. However, in the case of an aluminum deposited film, it becomes opaque; in the case of depositing an inorganic material, there is a disadvantage in that the production cost is increased due to a high deposition cost; and in the case of a polymer film with gas barrier properties, there is a problem that it is difficult to form a thin film.

Graphene has attracted much attention in recent years due to its high gas barrier function, as well as its mechanical, thermal, and electrical properties. Since graphene itself has gas barrier properties, it was expected that the above object could be achieved by using a graphene thin film or a graphene nanoplatelet formed through molecular deposition, but in terms of manufacturing costs and due to a low gas barrier performance, there are restrictions on commercial use.

Large-area graphene synthesized by deposition is considered as an ideal gas barrier material due to its high transparency and small pore diameter, which is smaller than the dynamic diameters of various gases. However, due to molecular structural defects that result from more or fewer carbon atoms besides benzene rings formed in the actual synthesis process, and due to physical defects such as tearing which may occur during the adhesion process of a synthesized large-area graphene film to a substrate, the gas barrier properties are reduced. Further, as the area to be formed becomes wider, expensive equipment and facilities corresponding to the wider area are necessary, and there are limitations to industrial manufacture such as increased manufacturing process cost, etc. Therefore, a method for synthesizing large-area graphene without defects and its application as a product are still difficult to achieve for these reasons, and there is a strong demand for a barrier film that can be easily industrially prepared as a replacement therefor.

In order to prepare a gas barrier film using graphene nanoplatelets exfoliated from graphite, graphene is mixed with a polymer to form a film, or graphene is modified so that it can be easily dispersed in a solvent by converting to graphene oxide (GO) having a hydroxyl, an epoxide, a carbonyl, and/or a carboxyl group, and the dispersion thereof is used as a coating solution.

In the case of the graphene nanoplatelet-polymer composite film, it forms 'tortuous channels' having a nano-barrier effect by a graphene nanoplatelet, which is dispersed in the polymer and has gas barrier properties, thereby forming a relatively long elongated gas diffusion path, which exhibits a reduction in the oxygen transmission rate (OTR). However, the content of the graphene nanoplatelet added in a polymer substrate for preparing a barrier film cannot be increased above a certain level, and the reduction rate of the oxygen transmission rate that can be achieved is limited due to the low dispersibility of the graphene nanoplatelets in the polymer substrate.

On the other hand, in the case of using a graphene oxide nanoplatelet with improved dispersibility with respect to the solvent, gaps between layered nanoplatelets exist, and as gas can permeate through the gaps, it is difficult to achieve gas barrier properties as expected, unless coated very thickly.

DISCLOSURE

Technical Problem

The present inventors have made efforts to find a method capable of remarkably improving an oxygen barrier function by coating with graphene oxide having an oxygen barrier function and an additive as described above, and completed the present invention by confirming that the oxygen barrier function was remarkably improved by coating by additionally comprising clay, which is an inorganic material, for example, plate-shaped clay.

Technical Solution

An object of the present invention is to provide a film comprising graphene oxide (GO) and clay.

Another object of the present invention is to provide an electronic device comprising the film as an oxygen barrier film.

Yet another object of the present invention is to provide a packaging material coated with the film as an oxygen barrier film.

A further object of the present invention is to provide a method for preparing a composite film comprising graphene oxide and clay, wherein the method comprises: a first step of preparing a graphene oxide dispersion; a second step of preparing a clay dispersion; a third step of mixing the two dispersions at a predetermined ratio followed by homogenization; and a fourth step of forming a film from the homogenized mixture solution.

A still further object of the present invention is to provide a method for preparing a multilayer film comprising graphene oxide and clay, wherein the method comprises: a first step of preparing a graphene oxide dispersion; a second step of preparing a clay dispersion; a third step of forming a first thin film with any one of the graphene oxide dispersion and the clay dispersion; and a fourth step of forming a second thin film on the first thin film with a dispersion other than the dispersion used in the third step.

Advantageous Effects

The film of the present invention comprising graphene oxide and clay can exhibit an excellent oxygen barrier function even with a thin thickness, and compared with conventional cases of using a composite material with an organic polymer in order to improve the oxygen barrier function, heat resistance can also be improved because the film comprises only inorganic materials, and therefore, it can be widely used as an oxygen barrier film in electronic devices, etc., or in packaging materials, etc. Further, since the film can be prepared by simple methods such as bar coating, it is suitable for mass production and large-area coating.

DESCRIPTION OF DRAWINGS

FIG. 1 shows images of PET films before and after coating with oxygen barrier films according to an exemplary embodiment of the present invention. From the left, (a) is an image of a PET film before coating, (b) is an image of a PET film coated with laponite (LN), (c) is an image of a PET film coated with graphene oxide (GO), and (d) is an image of a PET film coated with a graphene oxide/laponite (GO/LN) composite material. The right shows the flexibility of the PET film coated with GO/LN.

FIG. 2 shows a graph illustrating the oxygen transmission rates (OTR) of the PET films before and after coating with oxygen barrier films according to an exemplary embodiment of the present invention. As a negative control group, uncoated PET films, and as a positive control group, PET films coated only with each of laponite (LN) and graphene oxide (GO) were used. For experimental groups, each film was formed by bar coating a PET film with each composite material comprising GO and LN at ratios of 1.9:0.1 ($GO_{1.9}$/$LN_{0.1}$), 1.7:0.3 ($GO_{1.7}$/$LN_{0.3}$), and 1.5:0.5 ($GO_{1.5}$/$LN_{0.5}$), respectively.

FIG. 3 shows SEM images of the cross sections of the PET films coated with the oxygen barrier films according to an exemplary embodiment of the present invention. (A) shows a PET film coated with GO only, (B) shows a PET film coated with $GO_{1.9}$/$LN_{0.1}$, and (C) shows a PET film coated with $GO_{1.5}$/$LN_{0.5}$. Scale bars=100 nm.

FIG. 4 shows a graph illustrating the FT-IR spectra according to the pH or content of the components of the oxygen barrier films according to an exemplary embodiment of the present invention. (a) to (e) show the results corresponding to GO in order at pH 1.7, 2.3, 4.2, 5.5, and 12.0, respectively. (f) and (g) show the results corresponding to the GO/LN composite materials at $GO_{1.9}$/$LN_{0.1}$ and $GO_{1.5}$/$LN_{0.5}$, respectively. (h) and (i) show the results corresponding to LN at pH 9.8 and 5.2, respectively.

FIG. 5 shows the Raman spectra of the oxygen barrier films according to an exemplary embodiment of the present invention.

FIG. 6 shows the X-ray diffraction (XRD) patterns of the PET films coated with the oxygen barrier films according to an exemplary embodiment of the present invention. The oxygen barrier films were prepared using pure GO and GO/LN composite materials mixed with LN in various contents (1.9:0.1, 1.8:0.2, 1.7:0.3, 1.6:0.4, and 1.5:0.5).

FIG. 7 shows SEM images of the surfaces of the PET films coated with the oxygen barrier films according to an exemplary embodiment of the present invention. (A) to (D) show surface images of the PET films coated with GO only, and with the composite materials at $GO_{1.9}$/$LN_{0.1}$, $GO_{1.7}$/$LN_{0.3}$, and $GO_{1.5}$/$LN_{0.5}$, respectively. Scale bars=1 mm.

FIG. 8 shows AFM images of the surfaces of the PET films coated with the oxygen barrier films according to an exemplary embodiment of the present invention. (A) shows a surface coated with GO only, and (B) shows a surface coated with a GO/LN solution mixed with GO and LN at a volume ratio of 1.9:0.1.

FIG. 9 is a schematic diagram of the oxygen barrier films according to an exemplary embodiment of the present invention and the principle of blocking oxygen using the same.

BEST MODE

As one aspect for achieving the objects of the present invention, the present invention provides a film comprising graphene oxide (GO) and clay.

The present invention is based on a discovery that composite films or multilayer films comprising plate-shaped graphene oxide having a diameter of several tens of nanometers to tens of micrometers and clay having a nanometer-scale diameter can efficiently block oxygen even if they are prepared with thin films of several tens of nanometers.

As used herein, the term "graphene oxide" refers to a compound comprising carbon, oxygen, and hydrogen at various ratios, in which the carbon atoms are connected in a hexagon to form a plate-like shape, and the compound may comprise hydroxyl groups, which exist at an open end of the carbon plane and/or above or below the carbon plane, or an epoxide structure, in which two neighboring carbons are connected via oxygen. It is an analogue of graphene, and a material having a structure made of a single layer to several tens to several hundred layers from which can be obtained by treating graphite with a strong oxidizing agent to induce exfoliation between layers.

Preferably, the graphene oxide may be plate-shaped having an average diameter of 100 nm to 10 μm.

As used herein, the term "clay" refers to fine-grained soil comprising at least one mineral comprising a trace amount of metal oxides, and may be classified by size and/or mineralogy. In general, clay may exist in the form of a plate having a large surface area compared to the thickness, and may be composed of hedrons of silica and aluminum. As the clay of the present invention, natural clay, synthetic clay, or a mixture thereof can be used.

It is preferable that the clay is electrically-charged and thereby being water-dispersible. As described above, since graphene oxide is a material having excellent dispersibility in water, by using clay that is charged and dispersible in water, it is possible to easily obtain dispersions in which graphene oxide and clay are homogeneously distributed by simply mixing in an aqueous solution, followed by ultrasonic treatment. Further, preferably, the clay may be plate-shaped. Furthermore, the average diameter of the plate-shaped clay may be in a range of 10 nm to 500 nm. Graphene oxide is a plate-shaped material having an average diameter of several to several tens of micrometers, and when a film is formed with a composite material mixed with clay having a nanometer-scale diameter which is less than that of graphene oxide, the clay of the relatively small size can efficiently fill defects in graphene oxides or gaps between other graphene oxides. Non-limiting examples of such clay include cationic clay such as laponite (LN), montmorillonite (MMT), hectorite, saponite, beidellite, and nontronite; and anionic clay such as layered double hydroxide (LDH). The film of the present invention can be prepared by using any one of these clays, or by mixing two or more types thereof.

Preferably, the film may have a thickness of 10 nm to 500 nm. More preferably, the film may have a thickness of 20 nm to 200 nm, but is not limited thereto. If the thickness of the film is less than 10 nm, it may be difficult to obtain a sufficient effect of improving the oxygen barrier function to a desired degree, and if the thickness is more than 500 nm, the film is not only unnecessarily thickened, but also the rigidity of the film itself is increased to reduce the flexibility thereof, which may cause cracks due to impacts such as bending, etc., or may cause separation from the substrate or breakage.

Preferably, the film comprising graphene oxide and clay according to the present invention may be a film that consists of graphene oxide and clay, which does not further comprise an organic substance such as a polymer, etc. as a binder. Therefore, its durability is excellent even in harsh conditions such as a high temperature, etc., and since no additional constituents are required, it is possible to prepare a film exhibiting an excellent oxygen barrier function even as a thin film of several tens of nanometers.

The film comprising graphene oxide and clay according to the present invention may be 1) a composite film formed with a composite material comprising graphene oxide and clay, or 2) have a multilayer structure in which graphene oxide layers and clay layers, which are individually stacked, are alternated.

In particular, the composite material may comprise graphene oxide and clay at a weight ratio (wt/wt) in a range of 99:1 to 45:55. Alternatively, it may comprise graphene oxide and clay at a weight ratio (wt/wt) in a range of 95:5 to 45:55. Alternatively, it may comprise graphene oxide and clay at a weight ratio (wt/wt) in a range of 90:10 to 45:55, but is not limited thereto.

In the film comprising graphene oxide and clay according to the present invention, as shown in FIG. 9B, upper and lower adjacent graphene oxide layers form a layered structure, and the film can be prepared in a form in which clay is filled in gaps between the neighboring layers of graphene oxide in the outermost layer.

As a specific exemplary embodiment of the present invention, films were coated using a composite material comprising graphene oxide and clay at different ratios, and the oxygen transmission rates of each film were measured. As a result, it was confirmed that the effect of decreasing the oxygen transmission rate was dependent on the mixing ratio of graphene oxide and laponite, and specifically, a remarkable decrease in the oxygen transmission rate was confirmed in a film prepared with a composite material comprising graphene oxide and laponite at a weight ratio of 60:40, compared to a film prepared only with graphene oxide. On the other hand, it was confirmed that the effect of decreasing the oxygen transmission rate was not exhibited in films prepared with clay only, e.g., laponite, or with a composite material comprising graphene oxide and laponite at a weight ratio of 43:57 in which the laponite content is increased.

Preferably, the film comprising graphene oxide and clay according to the present invention is characterized in that it can exhibit an enhanced oxygen barrier function compared to a graphene oxide-only film or a clay-only film.

As another aspect, the present invention provides an electronic device comprising the film which comprises graphene oxide and clay as an oxygen barrier film.

Most electronic devices comprise metals with high electrical conductivity. However, these materials are sensitive to oxidation, i.e., reaction with oxygen. Therefore, it is preferable to coat with a film, etc. that is capable of blocking oxygen. Non-limiting examples of electronic devices requiring such an oxygen barrier film may include a battery, an organic light emitting device, a display device, a photovoltaic device, an integrated circuit, a pressure sensor, a chemical sensor, a biosensor, a solar device, and an illumination device.

As another aspect, the present invention provides a packaging material comprising the film which comprises graphene oxide and clay as an oxygen barrier film.

Metallic substances, food, nutritional supplements, etc. may react with oxygen in the air and oxidize. Therefore, currently, in order to extend a shelf life, a film deposited with aluminum or an inorganic substance, or a composite film stacked with a gas-barrier resin is used, but a packaging material comprising these may become opaque, the production cost may increase, and its thickness may be increased.

However, since the film of the present invention is not only capable of remarkably improving the oxygen barrier function, but also has excellent transparency and flexibility as well as an excellent barrier function even with a thin thickness, it is possible to reduce the thickness and to easily produce using existing coating equipment, and therefore, it is easy to prepare the film, and it can be used as a packaging material because it has a cost saving effect. Further, since it does not comprise organic substances such as a binder and comprises only inorganic substances, it can be expected that heat resistance is improved and the oxygen barrier function is maintained even at a high temperature. In particular, the packaging material may be formed by further comprising a substrate layer for maintaining the strength of the film of the present invention, a printed layer, a sealing layer for blocking water vapor, and/or a sealing layer for heat sealing; or may be coated on an existing packaging material.

As another aspect, the present invention provides a method for preparing a composite film comprising graphene oxide and clay, wherein the method comprises: a first step of preparing a graphene oxide dispersion; a second step of preparing a clay dispersion; a third step of mixing the two dispersions at a predetermined ratio followed by homogenization; and a fourth step of forming a film from the homogenized mixture solution.

Preferably, the solvent of the dispersion may be water. As described above, graphene oxide and clay have excellent dispersibility in water. In addition, water is a safe solvent which does not require considerations for toxicity or other factors compared with other organic solvents. Therefore, by using water as the solvent, factors such as cost, safety, etc. can be further improved.

The fourth step may be performed by bar coating, gravure coating, a slit coating, a comma coating, a spin coating, a spray coating, dip coating, or roll-to-roll coating. Preferably, the fourth step may be performed by bar coating on a substrate, but is not limited thereto. Bar coating is a coating method that can be most simply performed when using a solution, and it is a method that can be useful for mass production or large-area coating. However, the method for performing the fourth step is not limited thereto and can be achieved by using a coating method using a solution known in the art.

Preferably, the substrate may be a polyethylene terephthalate (PET) film, a polyethylene (PE) film, or a polypropylene (PP) film, but is not limited thereto. Films which are widely known to be used in the art can be used without limitation.

As a specific exemplary embodiment of the present invention, a single or mixed dispersion of GO and clay, which was prepared using water as a solvent, was bar-coated on a PET substrate as a coating solution. When an aqueous or hydrophilic solvent is used as described above, a substrate having a degree of hydrophilicity such as PET may be used for evenly applying the coating solution on the substrate. As such, since the substrate can be used by modifying through an appropriate pretreatment known in the art, any commercially available substrate can be used without limitation.

As another aspect, the present invention provides a method for preparing a multilayer film comprising graphene oxide and clay, wherein the method comprises: a first step of preparing a graphene oxide dispersion; a second step of preparing a clay dispersion; a third step of forming a first film with any one of the graphene oxide dispersion and the clay dispersion; and a fourth step of forming a second film on the first thin film with a dispersion other than the dispersion used in the third step.

Preferably, each of the third and fourth steps can be independently performed in order one or more times. Each of the third and fourth steps may be performed alternately several tens to several hundreds of times, and the number of repetitions is not limited as long as flexibility suitable for the purpose can be ensured, while achieving the desired oxygen barrier function. The number of repetitions may be determined by those skilled in the art by considering the thickness of each layer and the use of the final product.

In particular, each of the third and fourth steps may be independently performed by bar coating, applicator-coating, gravure coating, a slit coating, a comma coating, a spin coating, a spray coating, dip coating, or roll-to-roll coating, but is not limited thereto. Any method capable of introducing additional coating layers known in the art can be used without limitation.

MODE OF THE INVENTION

Hereinbelow, the present invention will be described in detail with accompanying exemplary embodiments. However, the exemplary embodiments disclosed herein are only for illustrative purposes and should not be construed as limiting the scope of the present invention.

EXAMPLE 1

Materials and Preparation of Thin Films

Highly concentrated graphene oxide dispersed in water (GO, 5 g/L, flake size: 0.5 μm to 5 μm, thickness: 1 atomic layer, at least 60%) was purchased from GRAPHENE SUPERMARKET (Calverton, N.Y., USA). Laponite (LN, RD grade) was purchased from ROCKWOOD ADDITIVES Ltd. (Widnes, Cheshire, UK) and used as it was. Polyethylene terephthalate (PET) films (TR55 and SG05, thickness: 100 μm, SKC, Seoul, Korea) without any chemical treatment were used as substrates. The pH of the GO solution and the LN solution was adjusted using hydrochloric acid (36.5% to 38.0%, SIGMA-ALDRICH) and sodium hydroxide (98%, SAMCHUN CHEMICALS).

EXAMPLE 2

Characterizations

Field emission scanning electron microscopy (FE-SEM) measurements were performed at 1 kV using SU-8020 (HITACHI, Tokyo, Japan). An ion milling system (IM4000, HITACHI, Tokyo, Japan) was used for the pretreatment process of the cross-sectional images at an acceleration voltage of 4 V and at a discharge current of about 415 μA while flowing argon gas at a flow rate of 0.17 cc/min. Oxygen transmission rates (OTR) were measured over an area of 50 cm$^2$ under a condition at a temperature of 23° C. and at a relative humidity of 0% using an oxygen permeation analyzer (OX-TRAN Model 702, MOCON, Minneapolis, Minn., USA) having a detection limit of 0.01 cc/m$^2$·atm·day. FT-IR and Raman spectroscopy were performed using Varian 660-IR (Varian medical systems, Inc., California, USA) and a SENTERRA Raman microscope spectrometer (BRUKER Corporation, Billerica, Mass., USA), respectively. X-ray diffraction (XRD) measurements were performed using SmartLab (Rigaku) at 40 kV and 30 mA (CuKα radiation, λ=0.154 nm) in a range of 1°<2θ<70°. Contact angle measurements were conducted using a contact angle analyzer (Phoenix 300, Surface Electro Optics Co., Ltd., Gyeonggi-do, Korea). Morphologies of the coated surface were analyzed at a scan rate of 0.5 Hz using an atomic force microscope (AFM) (NX10, Park Systems, Corp., Suwon, Korea) equipped with a noncontact cantilever.

EXAMPLE 3

Preparation of PET Films Coated with GO/Clay

After a GO dispersion (0.5 wt %) was ultrasonicated for 1 hour at an output of 50% using a chip-type ultrasonic generator (HD2200, BANDELIN electronic GmbH & Co. KG, Berlin, Germany), a GO-coated film was prepared by coating the GO dispersion on a film substrate using a bar coater (RDS bar coater #10). An LN-coated film was prepared by applicator-coating (200 μm) using an LN aqueous solution (4 wt %). For coating with a composite material comprising GO and laponite (LN), the GO dispersion and the LN aqueous solution (2 wt %) were mixed to provide a final volume ratio of GO to LN each at 1.9:0.1 ($GO_{1.9}$/$LN_{0.1}$), 1.8:0.2 ($GO_{1.8}$/$LN_{0.2}$), 1.7:0.3 ($GO_{1.7}$/$LN_{0.3}$), 1.6:0.4 ($GO_{1.6}$/$LN_{0.4}$), and 1.5:0.5 ($GO_{1.5}$/$LN_{0.5}$), followed by homogenization for 10 minutes using a waterbath-typed ultrasonic generator (ULTRASONIC3010, KODO Technical Research Co., Ltd., Gyeonggi-do, Korea). A PET film coated with the GO/LN composite material was prepared by bar coating (RDS bar coater #10) with the mixed dispersion. Further, instead of laponite, montmorillonite (MMT) was mixed with a GO solution at the same concentration and ratio, and a PET film coated with the GO/MMT composite material was prepared by coating in the same manner. Meanwhile, a multilayer coated PET film (DL-GO/LN) was prepared by coating with a GO dispersion (0.5 wt %, RDS bar coater #10), followed by applicator-coating using an LN aqueous solution (3 wt %, 200 μm applicator).

The composition and pH of the solutions used are shown in Table 1 below.

TABLE 1

| | Mixing ratio (v/v)* | | Weight ratio of solutes (wt/wt) | | pH of solution |
|---|---|---|---|---|---|
| | GO | LN | GO | LN | |
| GO | 2.0 | 0 | 100 | 0 | 2.3 |
| $GO_{1.9}/LN_{0.1}$ | 1.9 | 0.1 | 82.6 | 17.4 | 2.9 |
| $GO_{1.7}/LN_{0.3}$ | 1.7 | 0.3 | 58.6 | 41.4 | 4.4 |
| $GO_{1.5}/LN_{0.5}$ | 1.5 | 0.5 | 42.9 | 57.1 | 5.7 |
| LN | 0 | 2.0 | 0 | 100 | 9.8 |

*Solute content in solution: 0.5 (wt/v) % GO and 2 (wt/wt) % LN

<Result>

It was confirmed that the PET films coated with GO, LN, and GO/LN composite materials prepared in Example 3 were transparent and flexible. The PET films were photographed before and after coating and are shown in FIG. 1. As shown in FIG. 1, the film coated with LN alone was completely transparent similar to before coating, and the film coated with GO alone or with the GO/LN composite material was somewhat grayish but still transparent. Meanwhile, even though the films coated with the GO/LN composite materials did not comprise a polymeric binder, etc. and consisted of only inorganic materials, they were still flexible and easily bendable, and the exfoliation of the coating layer due to flexure did not occur.

In order to investigate the effect of the content of GO and clay on the oxygen barrier function of the composite materials, the composite materials which were prepared by mixing GO and LN each at different ratios were used for coating. GO platelets and LN discs having an average diameter of 0.5 µm to 5 µm and 25 nm, respectively, were used. Alternatively, MMT having an average diameter of 200 nm was used instead of LN.

In order to confirm the oxygen barrier function and its dependency on clay content of the GO/clay film of the present invention, uncoated PET films was used as a negative control group, PET films coated with either GO or LN were used as a positive control group, and PET films coated with composite materials each at different ratios of GO to clay were used as experimental groups. Two types of PET films, TR55 and SG05, having contact angles of 75.0° and 67.0°, respectively, were used, and laponite (LN) and montmorillonite (MMT) were used as clay. The oxygen transmission rates of the various non-coated/coated films were measured, the results for laponite are shown in FIG. 2, and the results for montmorillonite are shown in Table 2, respectively.

TABLE 2

| Sample | Relative humidity (RH, %) | OTRs (cc/m² · atm · day) |
|---|---|---|
| $GO_{1.9}/MMT_{0.1}$ | 0 | 0.8 ± 0.8 |
| $GO_{1.8}/MMT_{0.2}$ | 0 | 2.0 ± 0.3 |
| $GO_{1.7}/MMT_{0.3}$ | 0 | 2.1 ± 0.2 |
| $GO_{1.6}/MMT_{0.4}$ | 0 | 3.6 ± 0.3 |
| $GO_{1.5}/MMT_{0.5}$ | 0 | 3.9 ± 0.8 |

As shown in FIG. 2, TR55 films coated with pure GO or LN exhibited oxygen transmission rates (OTR) of 7.7 cc/m²·atm·day and 11.3 cc/m²·atm·day, respectively, which are slightly lower than or at a similar level with that of the uncoated film. On the basis of the above results, although the plate-shaped GO and LN discs, in themselves, are known as impermeable oxygen blocking materials, the oxygen barrier function of the film coated with a single component was still insufficient due to the atomic defects of GO itself, the occurrence of pinholes due to the formation of an incomplete stacked structure of GO, or undetectable fine cracks of LN, which allow oxygen to permeate during the drying process. Previous research suggested that a sufficiently thick GO layer such as GO paper can achieve a lower OTR value by offsetting defects or the occurrence of pinholes through tortuous channels and forming a longer path for oxygen molecule permeation. However, the coated films comprising GO and clay of the present invention were able to achieve significantly reduced oxygen transmission rates even with a relatively thin film of 50 nm (FIG. 3A).

The remarkable decrease in the OTR values as such was observed in all of the films coated with composite films prepared with the GO/LN composite materials and of the films coated with multilayer films prepared by sequentially stacking GO and LN layers. Particularly excellent effects for the oxygen barrier function were observed in films coated with a composite material comprising GO and LN, or GO and MMT each at a volume ratio of 1.9:0.1, that is, at a weight ratio of 82.6:17.4 (FIG. 2 and Table 2). In particular, the thickness of the coated film was only 59 nm (FIG. 3B). This indicates that even if the thickness of the coated film is thin, a thin film formed with a composite material, in which graphene oxide and clay are mixed at an appropriate ratio, can effectively block the entry and exit of oxygen gas. Simply, it can be expected that a $GO_{1.9}/LN_{0.1}$ thin film (about 59 nm) may exhibit a somewhat improved barrier function in that it has an increased thickness compared to the film coated with GO only (about 44 nm). As confirmed from FIGS. 2 and 3C, it was confirmed that there was a case in which it exhibited a lower barrier function depending on the composition ratio of the constituents, although a thicker layer was formed. Thus, it could be proven that the improved oxygen barrier function of the $GO_{1.9}/LN_{0.1}$ thin film compared to that of the GO-only-coated film was mainly due to the difference in the composite material and composition, not due to increased thickness.

Konkena et al. reported that the state of the functional groups of GO changes under various pH conditions and among the functional groups of GO, carboxyl groups exhibited pKa values of 4.3 and 6.6, and epoxy and hydroxyl groups exhibited a pKa value of 9.8. Further, an LN aqueous solution has a stable colloidal state in a high pH range, which is a basic condition, due to the formation of an electrical double layer inserted by sodium ions on the LN surface. On the other hand, sodium ions are substituted by the addition of $H^+$ ions, which causes shrinkage of the electrical double layer, allowing positive charges at the edges of the disc to interact with the negatively charged surface of the neighboring disc. Therefore, the functional groups of GO such as carboxyl, epoxy, and hydroxyl groups can have intermolecular or intramolecular interactions with the surface or the edges of LN, and this can be determined by the charge state under various pH conditions. In particular, the interactions between the Si—OH functional group of LN and the carboxyl and hydroxyl groups of the GO platelet may also be a driving force for LN attachments for defects in the GO layer.

In order to study the interactions between GO and LN, FT-IR and Raman spectra of the coated films were analyzed. The FT-IR and Raman spectra obtained from pure GO and LN, and the CO/LN composite films are shown in FIGS. 4 and 5, respectively. For the FT-IR measurement, the pH was adjusted to a desired pH using a concentrated hydrochloric acid solution or sodium hydroxide solution, for example, the GO solution was adjusted to pH 2.3, and the LN solution was adjusted to pH 9.8. For the layer coated with pure GO at pH 2.3, an intense band corresponding to the stretching mode of the carbonyl group (—C=O) of carboxylic acid (—COOH) appeared at 1722 $cm^{-1}$. And the asymmetric stretch of the carboxylate anion (—COO⁻) exhibited a vibration band at 1617 $cm^{-1}$. In addition, the peaks at 1421 $cm^{-1}$, 1052 $cm^{-1}$, and 968 $cm^{-1}$ represented C—O of the carboxyl group, C—O of the alkoxy or alkoxide group, and the epoxide group, respectively. As the pH increased, the band at 1722 $cm^{-1}$ due to carboxylic acid was decreased, and completely disappeared at pH 12. The C—O peaks on the carboxyl groups appeared at pH 4.2 and 5.5 shifted from 1421 $cm^{-1}$ to a range of 1373 $cm^{-1}$ to 1385 $cm^{-1}$ under acidic conditions of pH 1.7 and 2.2 due to the dehydrogenation of the carboxyl group. At pH 5.5, the weakening of hydrogen bonds was also accompanied by the shift of the C—O peaks due to the alkoxy or alkoxide group at 1052 $cm^{-1}$. For the GO/LN composite materials, $GO_{1.9}/LN_{0.1}$ (pH 2.9) and $GO_{1.5}/LN_{0.5}$ (pH 5.7) exhibited similar peak patterns. The peaks corresponding to the functional group of the carboxylic acid on GO shifted from 1722 $cm^{-1}$ to a range of 1716 $cm^{-1}$ to 1712 $cm^{-1}$ due to a change in the interaction induced by interactions with LN. Further, the alkoxy peak shifted to 1083 $cm^{-1}$, a new peak appeared at 1245 $cm^{-1}$, and this was due to the C—O vibrations of the epoxy/ether groups. Meanwhile, the peak at 1016 cm$^{-1}$ was due to the Si—O vibrations of amorphous silica. Compared with pure GO and LN-coated films, the changes in the peak positions in the FT-IR peak pattern of the composite materials indicate that the carboxyl, alkoxy, and epoxy groups of GO interacted with LN.

As shown in FIG. 5, in the Raman spectra obtained from the $GO_{1.9}/LN_{0.1}$ composite material, a distinct decrease in 2D peaks was observed. Meanwhile, GO showed distinct 2D peaks, and the shift of peaks from the G-band at 1583 cm$^{-1}$ of GO to 1591 cm$^{-1}$ of GO/LN and the shift of peaks from the D-band at 1349 cm$^{-1}$ of GO to 1355 cm$^{-1}$ of GO/LN were also confirmed. As previously reported, a decrease in the 2D peaks at about 2700 cm$^{-1}$, and the peak shifts of the G- and D-bands in the Raman spectra were caused by the doping and adsorption of charged impurities. This indicates that the LN discs were adsorbed to the GO surface, and in particular, a protected position by LN at defects and the edge position of GO blocked the delivery of gaseous molecules, thereby effectively extending the diffusion pathway. Meanwhile, the OTR values are known to be affected by the reduction state of GO. However, as shown in FIG. 5, the calculated $I_D/I_G$ value for GO/LN showed 0.89, which was similar to that for pure GO, and therefrom, it was confirmed that the change of the GO reduction state due to the addition of LN was not induced.

The X-ray diffraction (XRD) patterns of the films coated with the GO platelets and the LN discs were measured and are shown in FIG. 6. The XRD peaks corresponding to the films coated with pure GO and LN were found at 2θ=10.4° and 2θ=7.4°, respectively, which correspond to d-spacing of 0.85 nm and 1.19 nm, respectively. This is close to the interlayer distance (d-spacing) of about 0.83 nm which is shown in typical GO samples. On the other hand, the $GO_{1.9}/LN_{0.1}$ composite material showed only one peak, but $GO_{1.5}/LN_{0.5}$ with an increased clay content showed two peak patterns at 2θ=8.3° (small shoulder) and 2θ=11.3°.

The characteristic peak pattern of GO in the vicinity of 2θ=10° to 2θ=11° indicates that in the composite material solution, the LN discs attached to the surface of the GO platelet were desorbed from GO due to the relatively stronger face-to-face interaction between the GO platelets during the drying process. If the LN discs are attached between the GO platelets without desorption and thereby stacked, the d-spacing of the GO platelet must increase. Nonetheless, the desorption of LN can be expected if the d-spacing decreases rather than the GO itself. As it was confirmed that the LN discs were covering the outermost surface from the AFM image shown in FIG. 7, this indicates that LN was desorbed from the GO platelet during the drying process and the desorbed LN discs moved to the outermost layer of the stacked GO platelet and were attached thereto. Further, because the pH of the solution was increased as the content of LN in the composite material was increased, d-spacing was decreased due to stronger interactions between the GO platelets, and thus the largest 2θ value (the smallest d-spacing) was observed in $GO_{1.5}/LN_{0.5}$ which had the highest LN content. However, an increase in the oxygen transmission rates of $GO_{1.5}/LN_{0.5}$ which exhibited the smallest d-spacing was caused by restacking due to an agglomeration of the LN discs themselves, which occurred at θ=8.3°, and this was because an excess amount of restacked LN remaining even after covering the outermost surface of the stacked GO was inserted into gaps between the stacked faces of the GO platelets, and through the gaps a path was formed through which gas was permeated. Meanwhile, compared with the result for the peak of the pure LN sample at 2θ=7.4°, the shift of the peak at 2θ=8.3° of $GO_{1.5}/LN_{0.5}$ may be due to substitution of a sodium ion (Na$^+$) with a proton (H$^+$) caused by pH changes to acidic conditions in the composite material solutions.

In order to confirm such phenomenon, the surfaces of the composite material films with various compositions were studied by SEM. As shown in FIG. 8, GO wrinkles gradually disappearing in the GO/LN composite layers compared to pure GO were caused by an increase in the edge-to-edge distance between GO sheets, which was due to weaker edge-to-edge interaction between the GO sheets, and this was because the repulsion force was increased due to deprotonation of carboxyl groups at the edges of GO, as the pH of the composite coating solution was increased by adding a large amount of the LN solution with relatively high pH into the GO solution.

In FIG. 9, the mechanism for the oxygen barrier function of the film comprising GO and clay was shown by diagrams. Pure GO samples have a layered structure that exhibits edge-to-edge interaction based on carboxyl groups and face-to-face interaction based on alkoxy and epoxy groups (FIG. 9A). The addition of clay reduced the edge-to-edge interaction caused by the deprotonation of the carboxyl groups as the pH of the mixed solution was increased, and as the film was dried during the preparation thereof, plate-shaped discs which were attached to the surface of GO in the solution moved to the outermost surface of layered GO and induced such interactions. The clay discs on the outermost surface can block the transmission of oxygen molecules by filling the leaks or defects of GO. This was confirmed from the OTR values of the multilayer films (DL-GO/LN) of GO and clay. In the case of the multilayer films, clay particles of the clay layer and GO can interact and cap only at the outermost surface of the GO layer, not inside (FIG. 9). The OTR of the multilayer GO/clay film is at the lowest level of 0.31 cc/m$^2$·atm·day to 0.37 cc/m$^2$·atm·day, showing that more effective stacking of clay is possible only on the outermost surface of the layered GO due to a sufficient amount of clay coating to cover empty spaces. The addition of an excess amount of clay interferes with the edge-to-edge interaction of the GO platelets, and clay itself can be inserted into the gaps between the layered GO platelets.

Overall, it was confirmed that it is possible to easily prepare transparent and flexible films by solution casting using carbon-based GO and inorganic clay without organic additives. Compared with the OTR values of the films coated with pure GO, the composite films or multilayer films further comprising a small amount of clay exhibited an effect of significantly reducing the OTR even in thin films having a thickness of about 50 nm. It was confirmed that the improved oxygen barrier function as such was due to the formation of a dense barrier layer formed by the interaction of GO and clay on the outermost surface of the coated layer.

The invention claimed is:

1. A film comprising graphene oxide (GO) and clay in a structure having an enhanced oxygen barrier function compared to a graphene oxide film or a clay film of the same thickness,
   wherein the film does not comprise a binder,
   wherein the film has a thickness of 10 nm to 500 nm,
   wherein the film is a multilayer film having alternated layer of graphene oxide layers and clay layers, and
   wherein the film has a layered structure, in which upper and lower adjacent graphene oxide single layers are staggered, wherein the clay is filled in gaps between the neighboring graphene oxide single layers in the outermost layer.

2. The film of claim 1, wherein the graphene oxide is plate-shaped having an average diameter of 100 nm to 10 μm.

3. The film of claim 1, wherein the clay is electrically-charged and water-dispersible.

4. The film of claim 1, wherein the clay is plate-shaped.

5. The film of claim 1, wherein the clay is cationic clay, selected from the group consisting of laponite (LN), montmorillonite (MMT), hectorite, saponite, beidellite, and nontronite; anionic clay of layered double hydroxide (LDH); or a mixture thereof.

6. The film of claim 1, wherein the film consists of graphene oxide and clay.

7. An electronic device comprising the film according to claim 1 as an oxygen barrier film.

8. The electronic device of claim 7, wherein the electronic device is a battery, an organic light emitting device, a display device, a photovoltaic device, an integrated circuit, a pressure sensor, a chemical sensor, a biosensor, a solar device, or an illumination device.

9. A packaging material coated with the film according to claim 1 as an oxygen barrier film.

10. A method for preparing a multilayer film of claim 1 comprising graphene oxide and clay, the method comprising:
 a first step of preparing a graphene oxide dispersion;
 a second step of preparing a clay dispersion;
 a third step of forming a first thin film with one of the graphene oxide dispersion and the clay dispersion; and
 a fourth step of forming a second thin film on the first thin film with the other of the graphene oxide dispersion and the clay dispersion.

11. The method of claim 10, wherein the third and the fourth steps are each independently performed by bar coating, applicator-coating, gravure coating, a slit coating, a comma coating, a spin coating, a spray coating, dip coating, or roll-to-roll coating.

* * * * *